United States Patent
Esfandiari

(10) Patent No.: US 9,891,216 B2
(45) Date of Patent: Feb. 13, 2018

(54) IMMUNOASSAY METHODS UTILIZING TRAPPING CONJUGATE

(71) Applicant: Chembio Diagnostic Systems, Inc., Medford, NY (US)

(72) Inventor: Javanbakhsh Esfandiari, Stony Brook, NY (US)

(73) Assignee: CHEMBIO DIAGNOSTIC SYSTEMS, INC., Medford, NY (US)

( * ) Notice: Subject to any disclaimer, the term of this patent is extended or adjusted under 35 U.S.C. 154(b) by 0 days.

(21) Appl. No.: 14/631,006

(22) Filed: Feb. 25, 2015

(65) Prior Publication Data

US 2015/0285799 A1   Oct. 8, 2015

Related U.S. Application Data

(60) Provisional application No. 61/974,060, filed on Apr. 2, 2014.

(51) Int. Cl.
G01N 33/543 (2006.01)
G01N 33/558 (2006.01)
G01N 33/569 (2006.01)

(52) U.S. Cl.
CPC . *G01N 33/54386* (2013.01); *G01N 33/54366* (2013.01); *G01N 33/558* (2013.01); *G01N 33/56983* (2013.01); *G01N 33/56988* (2013.01); *G01N 2333/11* (2013.01); *G01N 2333/161* (2013.01); *G01N 2469/10* (2013.01); *G01N 2469/20* (2013.01)

(58) Field of Classification Search
CPC ........... G01N 33/54386; G01N 33/558; G01N 33/56983; G01N 33/56988
See application file for complete search history.

(56) References Cited

U.S. PATENT DOCUMENTS

| 3,960,488 A | 6/1976 | Giaever |
| 4,041,146 A | 8/1977 | Giaever |
| 4,042,335 A | 8/1977 | Clement |
| 4,059,405 A | 11/1977 | Sodickson et al. |
| 4,094,647 A | 6/1978 | Deutsch et al. |
| 4,144,306 A | 3/1979 | Figueras |
| 4,235,601 A | 11/1980 | Deutsch et al. |
| 4,313,734 A | 2/1982 | Leuvering |
| 4,323,536 A | 4/1982 | Columbus |

(Continued)

FOREIGN PATENT DOCUMENTS

| DE | 19917093 | 10/2000 |
| DE | 10313158 | 10/2004 |

(Continued)

OTHER PUBLICATIONS

"Testing for p24 Antigen," Centers for Disease Control and Prevention. Model Performance Evaluation Program. Human Immunodeficiency Virus Type 1 (HIV-1), 2002.

(Continued)

*Primary Examiner* — Melanie Yu Brown
(74) *Attorney, Agent, or Firm* — Gordon & Jacobson, P.C.

(57) ABSTRACT

Methods are provided for determining the presence of a first ligand in a sample. In some embodiments depletion conjugates are used to deplete the ligands different from but related to the first ligands from the sample. In some embodiments, interim binding agents are used to enhance the test signal.

2 Claims, 5 Drawing Sheets

(56) References Cited

U.S. PATENT DOCUMENTS

| | | |
|---|---|---|
| 4,361,537 A | 11/1982 | Deutsch et al. |
| 4,366,241 A | 12/1982 | Tom et al. |
| 4,373,932 A | 2/1983 | Gribnau |
| 4,522,786 A | 6/1985 | Ebersole |
| 4,532,107 A | 7/1985 | Siddigi |
| 4,588,555 A | 5/1986 | Provonchee |
| 4,595,654 A | 6/1986 | Reckel et al. |
| 4,632,901 A | 12/1986 | Valkirs et al. |
| 4,668,619 A | 5/1987 | Greenquist et al. |
| 4,703,017 A | 10/1987 | Campbell et al. |
| 4,740,468 A | 4/1988 | Weng et al. |
| 4,770,853 A | 9/1988 | Bernstein |
| 4,786,595 A | 11/1988 | Arai et al. |
| 4,826,759 A | 5/1989 | Guire et al. |
| 4,855,240 A | 8/1989 | Rosenstein et al. |
| 4,857,453 A | 8/1989 | Ullman et al. |
| 4,870,003 A | 9/1989 | Kortright et al. |
| 4,886,742 A | 12/1989 | Kortright et al. |
| 4,906,439 A | 3/1990 | Grenner |
| 4,912,034 A | 3/1990 | Kalra et al. |
| 4,920,046 A | 4/1990 | McFarland et al. |
| 4,943,522 A | 7/1990 | Eisinger et al. |
| 4,956,275 A | 9/1990 | Zuk et al. |
| 4,956,302 A | 9/1990 | Gordon et al. |
| 4,960,691 A | 10/1990 | Gordon et al. |
| 4,960,710 A | 10/1990 | Lau |
| 4,981,785 A | 1/1991 | Nayak |
| 4,981,786 A | 1/1991 | Dafforn et al. |
| 5,004,584 A | 4/1991 | Rayman |
| 5,006,464 A | 4/1991 | Chu et al. |
| 5,006,474 A | 4/1991 | Horstman et al. |
| 5,075,077 A | 12/1991 | Durley, III et al. |
| 5,087,556 A | 2/1992 | Ertinghausen |
| 5,091,153 A | 2/1992 | Bachand |
| 5,104,793 A | 4/1992 | Buck |
| 5,104,811 A | 4/1992 | Berger et al. |
| 5,110,550 A | 5/1992 | Schlipfenbacher |
| 5,132,208 A | 7/1992 | Freitag et al. |
| 5,137,808 A | 8/1992 | Ullman et al. |
| 5,147,780 A | 9/1992 | Pouletty et al. |
| 5,156,952 A | 10/1992 | Litman et al. |
| 5,162,238 A | 11/1992 | Eikmeier et al. |
| 5,169,789 A | 12/1992 | Bernstein |
| 5,173,433 A | 12/1992 | Bachand |
| 5,200,321 A | 4/1993 | Kidwell |
| 5,202,268 A | 4/1993 | Kuhn et al. |
| 5,215,446 A | 6/1993 | Takahashi |
| 5,217,905 A | 6/1993 | Marchand et al. |
| 5,219,762 A | 6/1993 | Katamine et al. |
| 5,223,436 A | 6/1993 | Freitag et al. |
| RE34,312 E | 7/1993 | Geiger et al. |
| 5,232,835 A | 8/1993 | Litman et al. |
| 5,238,649 A | 8/1993 | Nason |
| 5,240,735 A | 8/1993 | Lau |
| 5,244,631 A | 9/1993 | Morikawa |
| 5,244,788 A | 9/1993 | Hubscher |
| RE34,405 E | 10/1993 | Gould et al. |
| 5,252,496 A | 10/1993 | Kang et al. |
| 5,275,785 A | 1/1994 | May et al. |
| 5,281,540 A | 1/1994 | Merkh et al. |
| 5,296,192 A | 3/1994 | Carroll et al. |
| 5,300,439 A | 4/1994 | Charlton |
| 5,306,623 A | 4/1994 | Kiser et al. |
| 5,308,775 A | 5/1994 | Donovan et al. |
| 5,332,548 A | 7/1994 | Moore |
| 5,334,502 A | 8/1994 | Sangha |
| 5,338,513 A | 8/1994 | Schlipfenbacher |
| 5,340,748 A | 8/1994 | Baugher et al. |
| 5,356,782 A | 10/1994 | Moorman et al. |
| 5,362,654 A | 11/1994 | Pouletty |
| 5,369,007 A | 11/1994 | Kidwell |
| 5,384,264 A | 1/1995 | Chen et al. |
| 5,391,478 A | 2/1995 | Greene et al. |
| 5,399,316 A | 3/1995 | Yamada |
| 5,411,858 A | 5/1995 | McGeeham et al. |
| 5,418,136 A | 5/1995 | Miller et al. |
| 5,418,142 A | 5/1995 | Kiser et al. |
| 5,418,167 A | 5/1995 | Matner et al. |
| 5,424,215 A | 6/1995 | Albarella et al. |
| 5,424,220 A | 6/1995 | Goerlach-Graw et al. |
| 5,435,970 A | 7/1995 | Mamenta et al. |
| 5,451,504 A | 9/1995 | Fitzpatrick et al. |
| 5,468,648 A | 11/1995 | Chandler |
| 5,470,713 A | 11/1995 | El Shami et al. |
| 5,474,902 A | 12/1995 | Uylen et al. |
| 5,482,830 A | 1/1996 | Bogart et al. |
| 5,494,830 A | 2/1996 | Hubscher |
| 5,500,350 A | 3/1996 | Baker et al. |
| 5,501,985 A | 3/1996 | Baugher et al. |
| 5,514,557 A | 5/1996 | Moghaddam |
| 5,521,102 A | 5/1996 | Boehringer et al. |
| 5,532,133 A | 7/1996 | Barnwell |
| 5,541,057 A | 7/1996 | Bogart et al. |
| 5,550,063 A | 8/1996 | Bogart |
| 5,552,272 A | 9/1996 | Bogart |
| 5,558,834 A | 9/1996 | Chu et al. |
| 5,559,041 A | 9/1996 | Kang et al. |
| 5,567,594 A | 10/1996 | Calenoff |
| 5,571,667 A | 11/1996 | Chu et al. |
| 5,591,645 A | 1/1997 | Rosenstein |
| 5,602,040 A | 2/1997 | May et al. |
| 5,604,110 A | 2/1997 | Baker et al. |
| 5,607,863 A | 3/1997 | Chandler |
| 5,616,467 A | 4/1997 | Olsen et al. |
| 5,620,845 A | 4/1997 | Gould et al. |
| 5,622,871 A | 4/1997 | May et al. |
| 5,624,809 A | 4/1997 | Skold et al. |
| 5,629,164 A | 5/1997 | Rivers |
| 5,629,214 A | 5/1997 | Crosby |
| 5,639,671 A | 6/1997 | Bogart et al. |
| 5,641,639 A | 6/1997 | Perry |
| 5,648,274 A | 7/1997 | Chandler |
| 5,656,503 A | 8/1997 | May et al. |
| 5,658,723 A | 8/1997 | Oberhardt |
| 5,658,801 A | 8/1997 | Poissant et al. |
| 5,670,381 A | 9/1997 | Jou et al. |
| 5,686,315 A | 11/1997 | Pronovost |
| 5,695,928 A | 12/1997 | Stewart et al. |
| 5,695,930 A | 12/1997 | Weinstein et al. |
| 5,710,005 A | 1/1998 | Rittenburg |
| 5,714,341 A | 2/1998 | Thieme et al. |
| 5,714,389 A | 2/1998 | Charlton et al. |
| 5,723,345 A | 3/1998 | Yamauchi et al. |
| 5,726,010 A | 3/1998 | Clark |
| 5,728,587 A | 3/1998 | Kang et al. |
| 5,736,188 A | 4/1998 | Alcock et al. |
| 5,739,041 A | 4/1998 | Nazareth et al. |
| 5,743,960 A | 4/1998 | Tisone |
| 5,750,333 A | 5/1998 | Clark |
| 5,766,961 A | 6/1998 | Pawlak et al. |
| 5,766,962 A | 6/1998 | Childs et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,798,273 A | 8/1998 | Shuler et al. |
| 5,804,391 A | 9/1998 | Klemt et al. |
| 5,807,756 A | 9/1998 | Bauman et al. |
| 5,814,522 A | 9/1998 | Zimmer et al. |
| 5,824,268 A | 10/1998 | Bernstein et al. |
| 5,827,646 A | 10/1998 | Middeldorp et al. |
| 5,846,838 A | 12/1998 | Chandler |
| 5,853,670 A | 12/1998 | Bunce |
| 5,861,265 A | 1/1999 | Perry |
| 5,869,272 A | 2/1999 | Bogart et al. |
| 5,869,345 A | 2/1999 | Chandler |
| 5,872,713 A | 2/1999 | Douglas et al. |
| 5,874,216 A | 2/1999 | Mapes |
| 5,877,028 A | 3/1999 | Chandler et al. |
| 5,879,951 A | 3/1999 | Sy |
| 5,885,526 A | 3/1999 | Chu |
| 5,885,527 A | 3/1999 | Buechler |
| 5,891,650 A | 4/1999 | Godowski et al. |
| 5,900,379 A | 5/1999 | Noda et al. |
| 5,902,722 A | 5/1999 | Di Cesare et al. |

(56) References Cited

U.S. PATENT DOCUMENTS

| | | |
|---|---|---|
| 5,912,116 A | 6/1999 | Caldwell |
| 5,922,533 A | 7/1999 | Vallari et al. |
| 5,922,615 A | 7/1999 | Nowakowski et al. |
| 5,935,331 A | 8/1999 | Naka et al. |
| 5,939,252 A | 8/1999 | Lennon et al. |
| 5,939,272 A | 8/1999 | Buechler et al. |
| 5,948,695 A | 9/1999 | Douglas et al. |
| 5,955,377 A | 9/1999 | Maul et al. |
| 5,958,790 A | 9/1999 | Cerny |
| 5,965,458 A | 10/1999 | Kouvonen et al. |
| 5,972,720 A | 10/1999 | Nichtl et al. |
| 5,976,895 A | 11/1999 | Cipkowski |
| 5,985,675 A | 11/1999 | Charm et al. |
| 5,989,921 A | 11/1999 | Charlton et al. |
| 5,998,220 A | 12/1999 | Chandler |
| 5,998,221 A | 12/1999 | Malick et al. |
| 6,008,056 A | 12/1999 | Thieme |
| 6,017,767 A | 1/2000 | Chandler |
| 6,027,890 A | 2/2000 | Ness et al. |
| 6,040,195 A | 3/2000 | Carroll et al. |
| 6,046,013 A | 4/2000 | Tidey et al. |
| 6,046,057 A | 4/2000 | Nazareth et al. |
| 6,057,166 A | 5/2000 | Childs et al. |
| 6,060,326 A | 5/2000 | Frank et al. |
| 6,063,337 A | 5/2000 | Markart |
| 6,087,184 A | 7/2000 | Magginetti et al. |
| 6,106,732 A | 8/2000 | Johnston et al. |
| 6,140,134 A | 10/2000 | Rittenburg |
| 6,140,136 A | 10/2000 | Lee |
| 6,168,956 B1 | 1/2001 | Chandler |
| 6,187,268 B1 | 2/2001 | Albarella et al. |
| 6,187,598 B1 | 2/2001 | May et al. |
| 6,194,220 B1 | 2/2001 | Malick et al. |
| 6,197,494 B1 | 3/2001 | Oberhardt |
| 6,221,625 B1 | 4/2001 | Ashihara et al. |
| 6,221,678 B1 | 4/2001 | Chandler |
| 6,224,831 B1 | 5/2001 | Stafford et al. |
| 6,228,660 B1 | 5/2001 | May et al. |
| 6,235,464 B1 | 5/2001 | Henderson et al. |
| 6,248,598 B1 | 6/2001 | Bogema |
| 6,258,548 B1 | 7/2001 | Buck |
| 6,271,040 B1 | 8/2001 | Buechler |
| 6,271,045 B1 | 8/2001 | Douglas et al. |
| 6,271,046 B1 | 8/2001 | Chandler |
| 6,277,650 B1 | 8/2001 | Nazareth et al. |
| 6,284,550 B1 | 9/2001 | Carroll et al. |
| 6,287,875 B1 | 9/2001 | Geisberg |
| 6,297,020 B1 | 10/2001 | Brock |
| 6,297,060 B1 | 10/2001 | Nowakowski et al. |
| 6,300,142 B1 | 10/2001 | Andrewes et al. |
| RE37,437 E | 11/2001 | Friesen et al. |
| 6,316,205 B1 | 11/2001 | Guan et al. |
| 6,316,264 B1 | 11/2001 | Corey et al. |
| 6,319,676 B1 | 11/2001 | Nazareth et al. |
| 6,326,214 B1 | 12/2001 | Liu et al. |
| 6,335,205 B1 | 1/2002 | Bausback |
| 6,352,862 B1 | 3/2002 | Davis et al. |
| 6,362,008 B1 | 3/2002 | Kohn et al. |
| 6,368,875 B1 | 4/2002 | Geisberg |
| 6,368,876 B1 | 4/2002 | Huang et al. |
| 6,372,514 B1 | 4/2002 | Lee |
| 6,372,515 B1 | 4/2002 | Casterlin et al. |
| 6,372,516 B1 | 4/2002 | Sun |
| 6,376,195 B1 | 4/2002 | Mapes |
| 6,399,398 B1 | 6/2002 | Cunningham et al. |
| 6,403,383 B1 | 6/2002 | Casterlin et al. |
| 6,403,384 B1 | 6/2002 | Lea |
| 6,406,922 B2 | 6/2002 | Casterlin et al. |
| 6,413,473 B1 | 7/2002 | Bacon |
| 6,413,784 B1 | 7/2002 | Lundsgaard et al. |
| 6,436,722 B1 | 8/2002 | Clark et al. |
| 6,455,324 B1 | 9/2002 | Douglas |
| 6,472,226 B1 | 10/2002 | Barradine et al. |
| 6,475,805 B1 | 11/2002 | Charm et al. |
| 6,485,982 B1 | 11/2002 | Charlton |
| 6,489,129 B1 | 12/2002 | Faatz et al. |
| 6,492,127 B2 | 12/2002 | Goodell et al. |
| 6,500,629 B1 | 12/2002 | Cleaver et al. |
| 6,502,766 B1 | 1/2003 | Streutker et al. |
| 6,503,702 B1 | 1/2003 | Stewart |
| 6,503,722 B1 | 1/2003 | Valkirs |
| 6,511,814 B1 | 1/2003 | Carpenter |
| 6,514,769 B2 | 2/2003 | Lee |
| 6,514,773 B1 | 2/2003 | Klein et al. |
| 6,528,321 B1 | 3/2003 | Fitzgerald et al. |
| 6,528,322 B1 | 3/2003 | Carlsson et al. |
| 6,528,323 B1 | 3/2003 | Thayer et al. |
| 6,528,325 B1 | 3/2003 | Hubscher et al. |
| 6,534,324 B1 | 3/2003 | Zin |
| 6,544,474 B2 | 4/2003 | Douglas |
| 6,548,309 B1 | 4/2003 | Moore et al. |
| 6,551,842 B1 | 4/2003 | Carpenter |
| 6,592,815 B1 | 7/2003 | Zimmer |
| 6,593,085 B1 | 7/2003 | Barnett et al. |
| 6,602,719 B1 | 8/2003 | Carpenter |
| 6,617,116 B2 | 9/2003 | Guan et al. |
| 6,623,955 B2 | 9/2003 | Matner et al. |
| 6,627,459 B1 | 9/2003 | Tung et al. |
| 6,632,681 B1 | 10/2003 | Chu |
| 6,645,732 B2 | 11/2003 | Faatz et al. |
| 6,649,418 B1 | 11/2003 | Geisberg |
| 6,656,744 B2 | 12/2003 | Pronovost et al. |
| 6,656,745 B1 | 12/2003 | Cole |
| 6,660,469 B1 | 12/2003 | Wright et al. |
| 6,663,833 B1 | 12/2003 | Stave et al. |
| 6,673,628 B2 | 1/2004 | Freitag et al. |
| RE38,430 E | 2/2004 | Rosenstein |
| 6,686,167 B2 | 2/2004 | Bagaria |
| 6,699,722 B2 | 3/2004 | Bauer et al. |
| 6,703,196 B1 | 3/2004 | Klepp et al. |
| 6,706,539 B2 | 3/2004 | Nelson et al. |
| 6,713,309 B1 | 3/2004 | Anderson et al. |
| 6,727,073 B1 | 4/2004 | Moore et al. |
| 6,737,277 B1 | 5/2004 | Kang et al. |
| 6,750,031 B1 | 6/2004 | Ligler et al. |
| 6,753,190 B1 | 6/2004 | Okada et al. |
| 6,767,710 B2 | 7/2004 | DiNello et al. |
| 6,767,714 B2 | 7/2004 | Nazareth et al. |
| 6,780,651 B2 | 8/2004 | Douglas et al. |
| 6,790,611 B2 | 9/2004 | Lassen et al. |
| 6,797,481 B1 | 9/2004 | Ullman et al. |
| 6,808,889 B2 | 10/2004 | Fitzpatrick et al. |
| 6,808,937 B2 | 10/2004 | Ligler et al. |
| 6,812,038 B1 | 11/2004 | Mendel-Hartvig et al. |
| 6,818,180 B2 | 11/2004 | Douglas et al. |
| 6,818,455 B2 | 11/2004 | May et al. |
| 6,824,975 B2 | 11/2004 | Hubscher et al. |
| 6,824,997 B1 | 11/2004 | Moore et al. |
| 6,828,110 B2 | 12/2004 | Lee et al. |
| RE38,688 E | 1/2005 | Friesen et al. |
| 6,844,200 B2 | 1/2005 | Brock |
| 6,846,635 B1 | 1/2005 | Anderson et al. |
| 6,849,414 B2 | 2/2005 | Guan et al. |
| 6,855,561 B2 | 2/2005 | Jerome et al. |
| 6,863,866 B2 | 3/2005 | Kelly et al. |
| 6,867,051 B1 | 3/2005 | Anderson et al. |
| 6,887,701 B2 | 5/2005 | Anderson et al. |
| 6,905,835 B2 | 6/2005 | Sorell Gomez et al. |
| 6,924,153 B1 | 8/2005 | Boehringer et al. |
| 6,927,068 B2 | 8/2005 | Simonson et al. |
| 6,991,940 B2 | 1/2006 | Carroll et al. |
| 7,018,847 B2 | 3/2006 | Mendel-Hartvig et al. |
| 7,045,342 B2 | 5/2006 | Nazareth et al. |
| 7,049,130 B2 | 5/2006 | Carroll et al. |
| 7,109,042 B2 | 9/2006 | May et al. |
| 7,189,522 B2 | 3/2007 | Esfandiari |
| 7,270,995 B2 | 9/2007 | Matashshita et al. |
| 7,682,801 B2 | 3/2010 | Esfabdiari |
| 7,879,597 B2 | 2/2011 | Esfandiari |
| 8,507,259 B2 | 8/2013 | Esfandiari |
| 8,603,835 B2 | 12/2013 | Esfandiari |
| 2001/0012637 A1 | 8/2001 | Casterlin et al. |
| 2001/0026942 A1 | 10/2001 | Carpenter et al. |
| 2001/0026944 A1 | 10/2001 | Chung et al. |

(56) References Cited

U.S. PATENT DOCUMENTS

| | | |
|---|---|---|
| 2001/0034068 A1 | 10/2001 | Spivey et al. |
| 2001/0039057 A1 | 11/2001 | Douglas et al. |
| 2001/0048893 A1 | 12/2001 | Norris et al. |
| 2002/0001853 A1 | 1/2002 | Obremski et al. |
| 2002/0015663 A1 | 2/2002 | Goldstein et al. |
| 2002/0019062 A1 | 2/2002 | Lea et al. |
| 2002/0031839 A1 | 3/2002 | McNeirney et al. |
| 2002/0046614 A1 | 4/2002 | Alley |
| 2002/0048819 A1 | 4/2002 | Alley |
| 2002/0052050 A1 | 5/2002 | Douglas et al. |
| 2002/0057991 A1 | 5/2002 | Kelly et al. |
| 2002/0058330 A1 | 5/2002 | Carroll et al. |
| 2002/0110803 A1 | 8/2002 | Dhar et al. |
| 2002/0119497 A1 | 8/2002 | Wild et al. |
| 2002/0142291 A1 | 10/2002 | Bauer et al. |
| 2002/0155028 A1 | 10/2002 | Wong |
| 2002/0172937 A1 | 11/2002 | Dave et al. |
| 2002/0173050 A1 | 11/2002 | DiNello et al. |
| 2002/0192839 A1 | 12/2002 | Mink et al. |
| 2003/0045001 A1 | 3/2003 | Burgess et al. |
| 2003/0118480 A1 | 6/2003 | Kaylor et al. |
| 2003/0124740 A1 | 7/2003 | Bachand |
| 2003/0138351 A1 | 7/2003 | Etes et al. |
| 2003/0143639 A1 | 7/2003 | Matsushita et al. |
| 2003/0180967 A1 | 9/2003 | Shigetoh |
| 2004/0001767 A1 | 1/2004 | Peters et al. |
| 2004/0014157 A1 | 1/2004 | Sommer et al. |
| 2004/0087036 A1 | 5/2004 | Chung et al. |
| 2004/0142495 A1 | 7/2004 | Hartman et al. |
| 2004/0161859 A1 | 8/2004 | Guo et al. |
| 2004/0184954 A1 | 9/2004 | Guo et al. |
| 2004/0219694 A1 | 11/2004 | Chittock et al. |
| 2004/0235189 A1 | 11/2004 | Lu |
| 2004/0241779 A1 | 12/2004 | Piasio et al. |
| 2004/0248322 A1 | 12/2004 | Charlton |
| 2005/0074900 A1 | 4/2005 | Morgan et al. |
| 2005/0079629 A1 | 4/2005 | Guo et al. |
| 2005/0112779 A1 | 5/2005 | Wei et al. |
| 2005/0112780 A1 | 5/2005 | Song |
| 2005/0112782 A1 | 5/2005 | Buechler |
| 2005/0130293 A1 | 6/2005 | Blatt et al. |
| 2005/0130319 A1 | 6/2005 | Biegelsen et al. |
| 2005/0136500 A1 | 6/2005 | Yang et al. |
| 2005/0142032 A1 | 6/2005 | Hoenes et al. |
| 2005/0164404 A1 | 7/2005 | Marlborugh et al. |
| 2005/0170527 A1 | 8/2005 | Boehringer et al. |
| 2005/0208677 A1 | 9/2005 | Owens et al. |
| 2005/0227371 A1 | 10/2005 | Gokhan |
| 2005/0244985 A1 | 11/2005 | Freitag et al. |
| 2005/0244986 A1 | 11/2005 | May et al. |
| 2006/0099719 A1 | 5/2006 | Curcio |
| 2006/0121626 A1 | 6/2006 | Imrich |
| 2006/0134803 A1 | 6/2006 | Esfandiari |
| 2006/0148097 A1* | 7/2006 | Yamaguchi ......... G01N 33/558 436/514 |
| 2006/0166374 A1 | 7/2006 | Hubscher |
| 2007/0020768 A1 | 1/2007 | Rundstrom et al. |
| 2007/0059682 A1 | 3/2007 | Aberl et al. |
| 2007/0184492 A1 | 8/2007 | Wang et al. |
| 2007/0243630 A1 | 10/2007 | Boehringer et al. |
| 2008/0318341 A1 | 12/2008 | Esfandiari |
| 2009/0148933 A1 | 6/2009 | Batrell et al. |
| 2009/0181470 A1 | 7/2009 | Chiku et al. |
| 2010/0047857 A1* | 2/2010 | Fong ............... G01N 33/54313 435/39 |
| 2010/0112725 A1* | 5/2010 | Babu .................. G01N 33/558 436/518 |
| 2011/0124130 A1 | 5/2011 | Wagner et al. |
| 2011/0151584 A1 | 6/2011 | Esfandiari |
| 2012/0003727 A1 | 1/2012 | Esfandiari |
| 2012/0282154 A1 | 11/2012 | Slowey et al. |
| 2013/0225448 A1 | 8/2013 | O'Farrell |
| 2013/0309656 A1 | 11/2013 | Davis |
| 2014/0045172 A1 | 2/2014 | Esfandiari |

FOREIGN PATENT DOCUMENTS

| | | |
|---|---|---|
| EP | 0299359 | 1/1989 |
| EP | 1284422 | 2/2003 |
| EP | 2065706 | 6/2009 |
| JP | 05104052 | 4/1993 |
| WO | WO88/08534 | 11/1988 |
| WO | 199303175 | 2/1993 |
| WO | 199406013 | 3/1994 |
| WO | WO2004/084274 | 9/2004 |
| WO | WO2005/070324 | 8/2005 |
| WO | 2009075894 | 6/2009 |
| WO | WO 2013/105090 | 7/2013 |

OTHER PUBLICATIONS

A printout from http://en.wikipedia.org/wiki/P24 retreived on Oct. 2, 2012.

"An integrated microfluidic biochemical detection system for protein analysis with magnetic bead-based sampling capabilities," Choi et al., Lab Chip, 2002, 2, pp. 27-30.

Ho, David W. T., et al, Rapid Diagnosis of Acute Epstein-Barr Virus Infection by an Indirect Enzyme-Linked Immunosorbent Assay for Specific Immunoglobulin M (IgM) Antibody without Rheumatoid Factor and Specific IgG Interference; Journal of Clinical Microbiology, vol. 27, No. 5; May 1989, pp. 952-958, American Society for Microbiology.

Martins, Thomas B., et al., an Evaluation of the Effectiveness of Three Immunoglobulin G (IgG) Removal Procedures for Routine IgM Serological Testing; Clinical and Diagnostic Laboratory Immunology, Jan. 1995, vol. 2, No. 1; pp. 98-103; American Society for Microbiology.

* cited by examiner

H3 HA1 Microspheres

FIG. 2A

B/Bris HA1 Microspheres

FIG. 2B

IMMUNOASSAY METHODS UTILIZING TRAPPING CONJUGATE

CROSS-REFERENCE TO RELATED APPLICATION

This application claims benefit of U.S. Provisional Application Ser. No. 61/974,060, filed Apr. 2, 2014.

BACKGROUND

Related Patents

This application relates to co-owned U.S. Pat. Nos. 7,189,522, 7,682,801, 7,879,597, 8,507,259, and 8,603,835 all of which are hereby incorporated by reference herein in their entireties.

Field

The subject disclosure relates broadly to immunoassay methods and devices. More particularly, the subject disclosure relates to the detection of one or more particular ligands in a body fluid possibly containing additional related ligands.

State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Co-owned U.S. Pat. Nos. 7,189,522, 7,682,801, 7,879,597, and 8,507,259 are directed to improved rapid detection assays utilizing a "dual path" lateral flow device. More particularly, the immunoassay device is provided with a first sorbent strip that provides a first lateral or horizontal flow path for a conjugate, and a second sorbent strip that provides a second lateral or horizontal flow path for a sample. A test site having an immobilized ligand-binding mechanism is located on or in at least one of the strips, and the strips touch each other at the test site. In use, the sample and a buffer solution are first provided to the second sorbent strip and flow over time to the test site along the second flow path (i.e., they do not immediately wet the test site). If the sample contains ligand of interest, the ligand is captured at the test site by the immobilized ligand-binding mechanism. Buffer solution provided to the first sorbent strip carries the conjugate to the test site after the sample has reached the test site. If ligand is captured at the test site, the conjugate binds to the captured ligand and provides an indication of a "positive" test result; i.e., ligand of interest was present in the sample. If ligand is not captured at the test site, the conjugate does not bind, and a "negative" test results is obtained; i.e., ligand of interest was not present in the sample. A control line that captures conjugate may be provided near the test site to confirm that the test was properly conducted. By providing separate flow paths for the sample and the conjugate, substantially higher sensitivity and selectivity are obtained relative to standard lateral flow devices and reverse-flow devices utilizing single strips.

The dual path devices have also proved to be robust in providing accurate sensitive results where the test site is provided with multiple different immobilized ligand-binding mechanisms; i.e., multiplex capabilities. For example, separate test lines in a single DPP device have been provided for separately and accurately detecting HIV-1, HIV-2, and syphilis.

SUMMARY

In one embodiment a dual path immunoassay test cell device for detecting the presence of a first ligand in a sample is provided with a first sorbent material defining a first horizontal or lateral flow path and a second sorbent material defining a second horizontal or lateral flow path, the first and second sorbent materials overlying one another at a test site. The first flow path has a first location for receiving a first solution, which, in the case of a liquid conjugate system is a conjugate solution, and which, in the case of a dry conjugate system is a buffer solution. Where a buffer solution is utilized, the first sorbent material is provided with a first (mobile) conjugate located downstream of the first location. The second flow path has a second location for receiving a second solution comprising a sample. In one embodiment, the sample is a blood, urine, saliva, or other sample that may be mixed with buffer solution if desired, and immobilized second-ligand binding molecules are located downstream of the second location. The second-ligand binding molecules are related to the first ligand for which the sample is being tested but are not the same. The second sorbent material is distinct or separate from the first sorbent material. The test site is provided with first-ligand binding molecules such as immobilized antigens or antibodies or other molecules such as aptamers, nucleic acids, etc. located where the first and second sorbent materials overlie one another. The first-ligand binding molecules at the test site may be arranged in one or more lines or other distinctive patterns. A control line or site may be provided downstream from the test site.

In one embodiment, the second-ligand binding molecules are second conjugates that include immobilized ligand binding molecules conjugated with particles. In one embodiment, the second conjugate include antigens conjugated with particles. In one embodiment, the particles conjugated with the antigens comprise white latex. In another embodiment, the second conjugate includes antibodies conjugated with particles. In one embodiment, the particles conjugate with the antibodies comprise white latex. In one embodiment directed to detecting influenza ("flu"), the second-ligand binding molecules include antigens of at least one influenza ("flu") antigen and the test site is provided with immobilized antigen of at least one influenza antigen different but related to the at least one flu antigen of the immobilized conjugate. In one embodiment, the first conjugate is a gold sol conjugated to protein A.

In another embodiment a dual path immunoassay test cell device for detecting the presence of a first ligand in a sample is provided with a first sorbent material defining a first horizontal flow path and a second sorbent material distinct from the first sorbent material and defining a second horizontal flow path, the first and second sorbent materials overlying one another at a test site. The first flow path has a first location for receiving a first solution, which, in the case of a liquid conjugate system is a conjugate solution, and which, in the case of a dry conjugate system is a buffer solution. Where a buffer solution is utilized, the first sorbent material is provided with a first (mobile) conjugate located downstream of the first location. The second flow path has a second location for receiving a second solution comprising a sample such as blood, urine, saliva, or other sample that has been previously mixed with second-ligand binding molecules and, if desired, buffer and optionally filtered prior to being applied as the second solution to the second location. Where the sample has been mixed with second-ligand binding molecules and not filtered, in one embodiment, the second flow path may include a filter for the second solution. The second-ligand binding molecules are related to the first ligand for which the sample is being tested but are not the same and in one embodiment may include immobilized ligand binding molecules such as antigens or antibodies conjugated with particles such as latex. In one embodiment directed to detecting influenza ("flu"), the second ligand binding molecules include antigens of at least one influenza ("flu") antigen and the test site is provided with immobilized antigen of at least one influenza antigen different but related to the at least one flu antigen of the immobilized conjugate. In one embodiment the test site is provided with first-ligand binding molecules such as immobilized antigens or antibodies or other molecules such as aptamers, nucleic acids, etc. located where the first and second sorbent materials overlie one another. The first-ligand binding molecules at the test site may be arranged in one or more lines or other distinctive patterns. A control line or site may be provided downstream from the test site.

In one aspect, the second-ligand binding molecules are used as a depleting mechanism that captures and thereby depletes antibodies (or antigens) related to the antibodies (or antigens) that are being detected at the test site. By way of example, where the test site includes a pendemic flu-A antigen for identifying the presence of a flu-A antibody in the sample, the second conjugate may be provided with one or more common flu-A antigens and or flu-B antigens. In this manner, common flu-A and flu-B antibodies in the sample that may otherwise be captured or retained at the test site (because of their structure which can be similar in many ways to the related pandemic flu-A antibodies) are generally captured by the second immobilized conjugate; i.e., the number of common flu-A and flu-B antibodies reaching the test site is depleted. As a result, the sensitivity of the test is increased.

In one aspect, the use of a white latex conjugate as the immobilized depleting conjugate reduces the visibility of the conjugate should it be loosened and travel with the sample to the test site and arrive at the test site.

Where the test cell is provided in a housing, the housing is provided with a first opening adjacent the first location and a second opening adjacent the second location. A viewing window is provided in the housing above the test line. Similarly, a viewing window may be provided in the housing above the control line.

According to one set of embodiments, the sorbent materials are laid out in a T shape, where the first location for receiving the buffer or buffer-conjugate solution is located near one end of the top bar of the T, the second location for receiving the sample is located near the end of the stem of the T, and the sorbent materials overlie each other at the intersection. Of course, the sorbent materials may be laid out in other configurations, and the housing may take other shapes, such as rectangular, square, irregular, etc. regardless of the manner in which the sorbent materials are arranged.

In one embodiment of the invention, the materials, thicknesses and lengths of the first and second sorbent materials are chosen to adjust the timing regarding the liquid sample and liquid buffer reaching the test site.

In the dry conjugate system, a first dry conjugate is provided between the first opening and the test site. The first conjugate is supported on or within the sorbent material such that when a buffer is added in the first opening, the sorbent material wicks the buffer to the first conjugate which is then carried by the buffer to the test site. In the liquid conjugate system, a buffer-conjugate liquid subsystem is provided and applied to the first opening. The sorbent material then wicks the buffer-conjugate subsystem to the test site.

In another embodiment a dual path immunoassay test cell device for detecting the presence of a first ligand in a sample is provided with a first sorbent material defining a first horizontal flow path and a second sorbent material distinct from the first sorbent material and defining a second horizontal flow path, the first and second sorbent materials overlying one another at a test site. The first flow path has a first location for receiving a first solution, which, in the case of a liquid conjugate system is a conjugate solution, and which, in the case of a dry conjugate system is a buffer solution. Where a buffer solution is utilized, the first sorbent material is provided with a first (mobile) conjugate located downstream of the first location. The first conjugate includes a marker such as a colored latex or particle and a first interim binding agent such as (by way of example only) streptavidin or an anti-biotin antibody. The second flow path has a second location for receiving a second solution comprising a sample such as blood, urine, saliva, or other sample that has been optionally previously mixed with second-ligand binding molecules and, if desired, buffer and is optionally filtered to remove the second-ligand binding molecules and second ligand bound thereto prior to being applied as the second solution to the second location. The second flow path is provided with immobilized first-ligand binding molecules. The immobilized first-ligand binding molecules may include a second conjugate of latex particles (e.g., white latex) to which are bound antibodies or antigens and a second interim binding agent such as biotin. In this manner, when the sample includes the first ligand, the first-ligand binding molecules with the first ligand and second interim binding agent attached thereto are carried by the filtered sample solution to the test site along the second flow path. The test site which is located where the first and second sorbent materials overlie one another is provided with an immobilized binding agent which bind to the antigen or antibodies of the sample. Thus, the ligand with the second interim binding agent is bound at the test site, and when the first conjugate travels down the first flow path with the colored latex or particle and first interim binding agent, the interim binding agents will attach and keep the colored latex at the test site. A control line or site may be provided downstream from the test site.

In one aspect, where the first flow path is provided with a conjugate having a the second flow path is provided with immobilized first-ligand binding molecules with a second interim binding agent and the first test line is provided with a conjugate having a first interim binding agent, and sensitivity of the test is enhanced.

According to one method, a system for detecting the presence of a first ligand in a sample is provided and includes a test cell having a first sorbent material having a first location for receiving a buffer solution (in the case of a dry conjugate system) or a conjugate solution (in the case of a liquid conjugate system) with the first sorbent material defining a first horizontal flow path, and a second sorbent material having a second location for receiving a sample and defining a second horizontal flow path distinct from the first flow path, with the second sorbent material having a second-ligand binding molecules located downstream of the second location, and a test line or test site with immobilized first-ligand binding molecules such as antigens, antibodies, aptamers, nucleic acids, etc. located in a test zone at a junction of the first and second sorbent materials. If desired, a housing is also provided having a first opening for receiving the buffer or conjugate solution, a second opening for receiving the sample, and a viewing window above the test line. A sample of interest is provided to the second opening or location and permitted to migrate down to the test line over time. After a desired amount of time, a liquid such as a buffer solution is added to the first opening or location. If the first sorbent material is supporting a conjugate (i.e., in a dry conjugate system), the liquid can be simply a buffer solution. If the first sorbent material is not supporting a conjugate (i.e., in a liquid conjugate system), the liquid can be a buffer-conjugate liquid subsystem. In any event, after sufficient time to permit the first conjugate to migrate to the test site (and control site if provided), the test site (and control site if provided) is inspected in order to determine whether the sample is "positive" or not.

According to another method, a system for detecting the presence of a first ligand in a sample is provided and includes a test cell having a first sorbent material having a first location for receiving a buffer solution (in the case of a dry conjugate system) or a conjugate solution (in the case of a liquid conjugate system) with the first sorbent material defining a first horizontal flow path, and a second sorbent material having a second location for receiving a sample and defining a second horizontal flow path distinct from the first flow path with an optional filter, and a test line or test site with immobilized first-ligand binding molecules such as antigens, antibodies, aptamers, nucleic acids, etc. located in a test zone at a junction of the first and second sorbent materials. If desired, a housing is also provided having a first opening for receiving the buffer or conjugate solution, a second opening for receiving the sample, and a viewing window above the test line. A sample of interest is provided to a mixing chamber having second-ligand binding molecules and optional buffer. The sample is mixed with the second-ligand binding molecules (and buffer) and optionally filtered to remove the second-ligand binding molecules and second ligand attached thereto if the second flow path has no filter. The optionally filtered sample is provided to the second opening or location and permitted to migrate along the second flow path down to the test site. After a desired amount of time, a liquid such as a buffer solution is added to the first opening or location. If the first sorbent material is supporting a conjugate (i.e., in a dry conjugate system), the liquid can be simply a buffer solution. If the first sorbent material is not supporting a conjugate (i.e., in a liquid conjugate system), the liquid can be a buffer-conjugate liquid subsystem. In any event, after sufficient time to permit the first conjugate to migrate to the test site (and control site if provided), the test site (and control site if provided) is inspected in order to determine whether the sample is "positive" or not.

According to another method, a system for detecting the presence of a first ligand in a sample is provided and includes a test cell having a first sorbent material having a first location for receiving a buffer solution (in the case of a dry conjugate system) or a conjugate solution (in the case of a liquid conjugate system) with the first sorbent material defining a first horizontal flow path for a first conjugate having a marker and a first interim binding agent, and a second sorbent material having a second location for receiving a sample and defining a second horizontal flow path distinct from the first flow path with immobilized first-ligand binding molecules such as antibody or antigen bound to a second interim binding agent, and a test line or test site with immobilized binding agent located in a test zone at a junction of the first and second sorbent materials. If desired, a housing is also provided having a first opening for receiving the buffer or conjugate solution, a second opening for receiving the sample, and a viewing window above the test line. A sample of interest is optionally provided to a mixing chamber having second-ligand binding molecules and optional buffer. The sample may be mixed with the second-ligand binding molecules (and buffer) and filtered to remove the second-ligand binding molecules and second ligand attached thereto. The optionally filtered sample is provided to the second opening or location and may then interact with a second conjugate having a second interim binding agent as it migrates along the second flow path to the test site. After a desired amount of time, a liquid such as a buffer solution is added to the first opening or location. If the first sorbent material is supporting a first conjugate (i.e., in a dry conjugate system), the liquid can be simply a buffer solution. If the first sorbent material is not supporting a conjugate (i.e., in a liquid conjugate system), the liquid can be a buffer-conjugate liquid subsystem containing the first conjugate. In any event, after sufficient time to permit the second conjugate to migrate to the test site (and control site if provided), the test site (and control site if provided) is inspected in order to determine whether the sample is "positive" or not.

It will be appreciated that the systems can be used in conjunction with different types of samples such as blood, urine, saliva, etc. The sample may be diluted or mixed with buffer prior to being added through the second hole. Alternatively, in some cases, the sample may be added through the hole and then a diluent may be added through the same hole.

Objects and advantages will become apparent to those skilled in the art upon reference to the detailed description taken in conjunction with the provided figures.

BRIEF DESCRIPTION OF THE DRAWINGS

FIG. 2A is a chart comparing test results of the apparatus of FIG. 1 against the test results of a standard dual path platform apparatus and showing the depletion of non-pandemic flu antibodies by the apparatus of FIG. 1

FIG. 2B is a chart comparing test results of the apparatus of FIG. 1 against the test results of a standard dual path platform apparatus and showing non-depletion of flu-B antibodies by the apparatus of FIG. 1.

DETAILED DESCRIPTION

Figure 1:
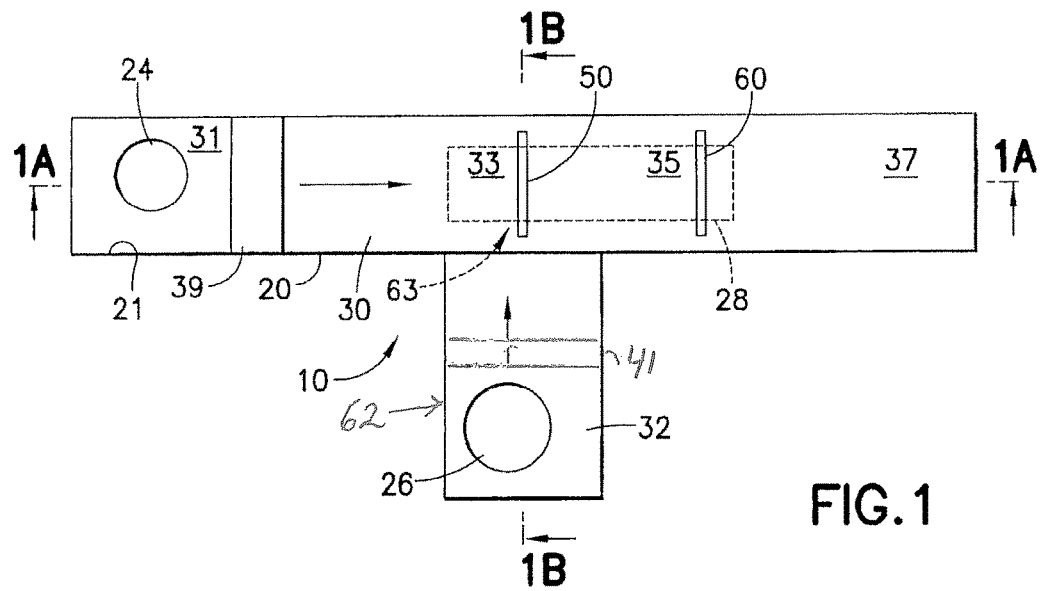
FIG. 1 is a top schematic view of a first embodiment.
Figure 1A:
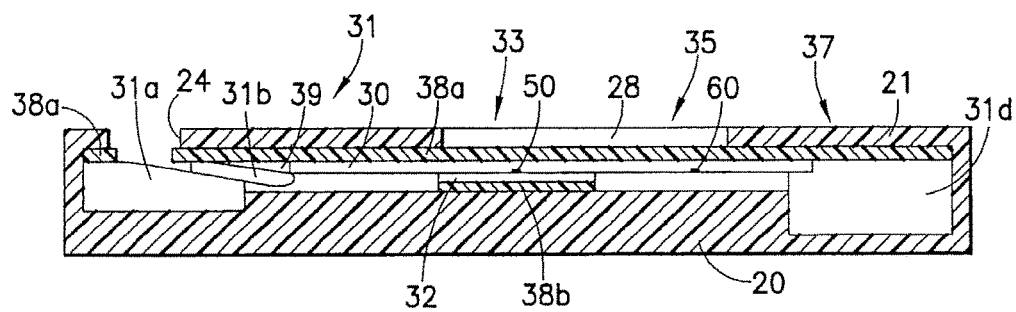
FIG. 1A is a cross-sectional view taken along line 1A-1A of FIG. 1.
Figure 1B:
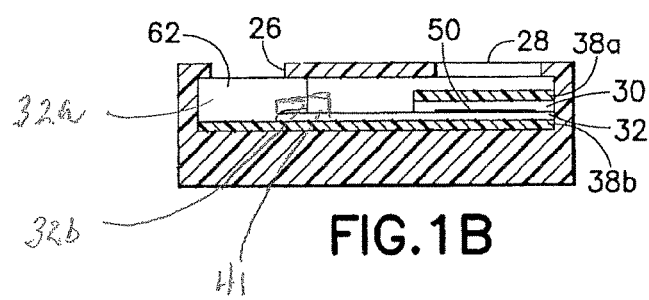
FIG. 1B is a cross-sectional view taken along line 1B-1B of FIG. 1.
Figure 3:
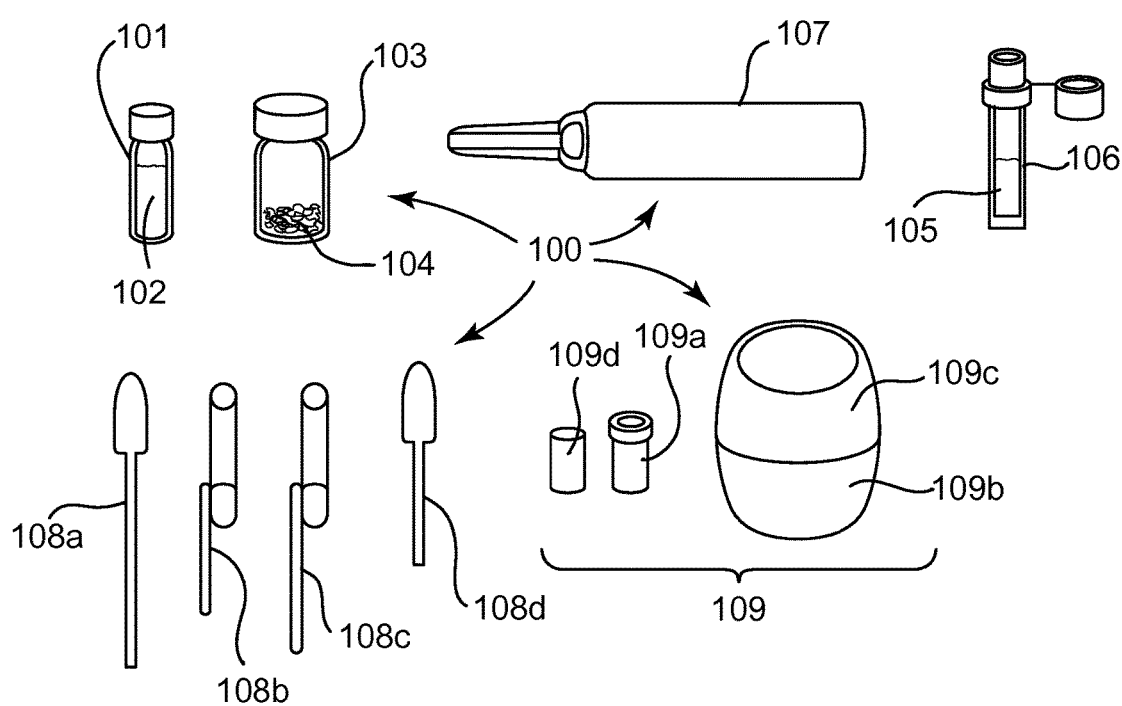
FIG. 3 is a diagram showing a kit including a water vial, a vial with conjugate, a vial with diluent, a blood collection and transfer device, three transfer pipettes, and a filter chamber.

Turning now to FIGS. 1, 1A and 1B, an immunoassay device test cell 10 for testing for the presence of a first ligand in a sample is provided and includes a housing 20 having a top wall 21 defining first and second holes 24, 26, and a window 28, and first and second sorbent or bibulous materials 30, 32 defining perpendicular horizontal or lateral flow paths in the housing. The first sorbent material 30 includes a plurality of zones and may be made from a plurality of materials. A first zone 31 (sometimes called a filter zone) is located at the first hole 24 and extends to a second zone 33 (sometimes called a test zone) which is located at the junction of a "T". The first zone 31 preferably includes a filter 31a, a pad 31b on or in which a conjugate 39 having desired antigens or antibodies with attached colored markers is deposited and immobilized, and a first portion of a thin membrane or sorbent or bibulous material 30 typically made from nitrocellulose with a plastic backing (not shown). In one embodiment, and by way of example only, conjugate 39 may be a gold sol conjugated to protein A. The first zone 31 is adapted to receive a buffer solution, to cause the buffer solution to contact the conjugate, thereby mobilizing the conjugate, and to wick the conjugate-carrying buffer solution to the second zone 33. The second (test) zone 33 includes a second portion of the thin membrane 30 which can be printed with a test line 50 having immobilized first ligand binding molecules such as antigens or antibodies (depending on whether the test cell is designed to test for the presence of antibodies or antigens) on the membrane as is well known in the art. The test line 50 may be seen through the window 28 of clear plastic provided in the housing. A third zone 35 (sometimes called a control zone) which includes a third portion of the thin membrane 30 may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, the window 28 extends above the control line 60. If desired, a fourth zone 37 (sometimes called a reservoir zone) may be provided as a wicking reservoir as is also well known in the art. The fourth zone 37 includes a relatively thicker absorbent paper. Preferably overlying all the zones is a thin, preferably transparent plastic film or card 38a having an adhesive which keeps the sorbent materials in place. The card 38a may be cut with an opening at hole 24 so that it does not block liquid access to the hole 24.

The second sorbent material 32 may also be made from a plurality of materials and include a plurality of zones. The first zone 62 (sometimes called a filter zone) includes a filter or pad 32a and a pad 32b on or in which second-ligand binding molecules are provided and immobilized, where the second ligand is different than but related to the first ligand, and a first portion of a thin membrane or sorbent or bibulous material 32 typically made from nitrocellulose with a backing (not shown). The second-ligand binding molecules may include antigens or antibodies or other molecules such as aptamers, nucleic acids, etc. that bind to ligands that are similar to but different than the first ligands. The second-ligand binding molecules may be provided as a conjugate 41 having desired antigens or antibodies with attached particles. The first zone 62 is located at the second hole 26 and extends to the second zone 63. The second zone 63 includes a second portion of the thin membrane 32 which is in contact with the second zone 33 of the first sorbent material 30. As is seen in FIGS. 1A and 1B, the first sorbent material 30 overlies the second sorbent material 32 such that the membranes are in contact with each other (as opposed to the backings contacting the membranes or each other), and such that the test line 50 is effectively located between the membranes. Thus, test line 50 could be printed on the second zone 63 of the second sorbent material 32 instead of, or in addition to the second zone 33 of the first sorbent material 30. If desired, a thin plastic film or card 38b having an adhesive which keeps the second sorbent material in place may be utilized. With the provided arrangement it takes time for the sample to travel from its application point to the second zone 63 and the test site, and application of sample to the second flow path does not immediately wet the test site.

In one embodiment the conjugate 41 on the conjugate pad 32b includes antigens conjugated with a particle that is not readily visible to the human eye against the background of the test area. In one embodiment, the particle is a white latex. One embodiment of a white latex is a 0.32 micron white latex bead available from Thermo Fisher Scientific, Inc., Holtsville, N.Y. The antigens of conjugate 41 are different than but are related to the antigens of test line 50. By way of example only, in an embodiment directed to detecting pandemic influenza ("flu"), the second conjugate includes antigens of at least one influenza ("flu") antigen (e.g., two different flu A antigens such as H1 and H3 flu antigens) and the test site is provided with immobilized antigen of at least the pandemic influenza antigen of interest which is different from but related to the at least one flu antigen of the immobilized conjugate 41. In another embodiment, the second conjugate includes antibodies conjugated with white latex and the test site 50 includes antibodies different than but related to the antibodies of the conjugate 41.

In one aspect, the second conjugate is used as a depleting mechanism that captures and thereby depletes antibodies related to the antibodies that are being detected at the test site. By way of example, where the test site includes a flu-B antigen for identifying the presence of a flu-B antibody in the sample, the second conjugate may be provided with one or more flu-A antigens; i.e., there may be a plurality of slightly different second conjugates. In this manner, flu-A antibodies in the sample that may otherwise be captured or retained at the test site (because of their structure which can be similar in many ways to the related flu-B antibodies) are generally captured by the second immobilized conjugate; i.e., the number of flu-A antibodies reaching the test site is depleted. As a result, the sensitivity of the test is increased. It will be appreciated that the test site could include a flu-A antigen for identifying the presence of a particular flu-A antibody in the sample, and the second conjugate may be provided with one or more flu-B antigens and one or more flu-A antigens that are different from but related to the particular flu-A antigen at the test site. Further, it will be appreciated that the test site may be provided with more than one test line, containing different flu antigens. Those flu antigens could include a plurality of flu-A antigens, a plurality of flu-B antigens, or one or more flu-A and one or more flu-B antigens. The second immobilized conjugate will be adjusted accordingly to include conjugate that will deplete those antigens that are related to the antigens of the test lines but are not the subject of the test.

In one aspect, the use of a white latex conjugate as the immobilized depleting conjugate reduces the visibility of the conjugate should it be loosened and travel with the sample to the test site and get captured at the test site. In another aspect, latex beads of a size larger than the pore size of the second migration path may be utilized in order to prevent movement of the conjugate along the second migration path.

Where standard-type nitrocellulose strips with a backing are utilized as the first and second membranes, the membranes can have different pore sizes. For example, if membrane 31 (for the first conjugate migration) has a 3μ pore size, and membrane 32 (for the sample migration) has a 15μ pore size, sample applied to membrane 32 will tend to migrate and stay in the sample membrane 32 and will tend not to migrate into the conjugate membrane 31.

The immunoassay of FIGS. 1, 1A and 1B is preferably utilized as follows. First, a sample (not shown) possibly containing antibodies (or antigens) is optionally diluted (e.g., with buffer) and provided to the second opening or hole 26. The sample does not immediately wet the test site but is allowed to take time to migrate from pad 32a to conjugate pad 32b and then from zone 61 of the second sorbent material 32 to its second zone 63 which is contact with the second zone 33 of the first sorbent material 30. If the sample is not first diluted, optionally, after providing the sample to hole 26, a measured amount of liquid such as a buffer solution may be added to hole 26 to help in the migration of the sample. Regardless, if the sample includes antigens or antibodies that react with the second conjugate 41 of conjugate pad 32b, those antigens or antibodies are captured by the conjugate 41 and are depleted from the sample before reaching the test line 50 which is printed atop the second zone 33 of the first sorbent material or infused therein. To the extent that the conjugate 41 loosens from the pad 32b and travels along membrane 32 down to the test site and is captured there, the conjugate 41 will not be particularly visible because the white latex particles will not be seen on the white background of the test site. Regardless, after a desired amount of time, by which time the antibodies (or antigens) in the sample (if present) will have had an opportunity to bind to the antigens (or antibodies) immobilized at the test line 50, a liquid such as a buffer solution (not shown) is added to the first opening 24. After another period of time, sufficient to permit the buffer solution to cause the conjugate to migrate to the test site 50 (and control site 60 if provided), and to bind with the antigens (or antibodies) of the sample that are captured at the test site 50 (if any), the test site (and control site 60 if provided) is inspected via window 28 in order to determine whether the sample is "positive" or not. Typically, a "positive" test indicating the presence of the antibody (or antigen) in the sample is obtained when both the test site 50 and the control site 60 show lines of color. A "negative" test indicating the lack of the presence of the antibody (or antigen) in the sample is obtained when only the control site 60 shows a line of color.

The use of the apparatus may be expedited by providing the housing with numbering and/or lettering to indicate that hole 26 is for receiving the sample (and optionally some buffer) and is to be used first, and that hole 24 is for receiving the buffer solution and is to be used second.

Those skilled in the art will appreciate that the immunoassay 10 functions as follows. Because the test line 50 is provided with antigens (or antibodies) immobilized on a membrane, if the test sample contains antibodies to the antigens (or antigens to the antibodies), the antibodies (or antigens) will bind themselves to the antigens (or antibodies) at the test line. Because the test sample passes through a conjugate pad 32b having immobilized second conjugate 41 with antigens (or antibodies) that are related to but different than the antigens (or antibodies) of the test line, related antibodies or antigens to those being tested, if present, will be captured by the conjugate 41 and held at the conjugate pad 32b, and when the test sample reaches the test line, the antibodies (or antigens) of the sample, if present, will bind to the antigen (or antibody) at the test line. Because the related antibodies (or antigens) are depleted, they will not reach the test line, and if they do, they will already be conjugated with a latex that will reduce their activity at the test site. Regardless, the test site will be more specific to the antibodies or antigens whose presence is to be detected. After the sample has reached the test site, the first conjugate 39 containing an antigen for the antibody (or antibody for the antigen) coupled to a colored marker is caused to migrate to the test line. If the test sample contains the antibodies (or antigens) which are now held at the test line 50, the antigen (or antibody) of the conjugate will bind itself to the antibodies (or antigens) and the colored marker will cause a colored line to appear at the test site 50. If the test sample does not contain antibodies (or antigens), the conjugate will not have the antibodies (antigens) to bind to at the test line 50, and no colored line will appear at the test site 50. On the other hand, because the control line 60 is provided with antibodies (or antigens), the antigens (or antibodies) of the conjugate will always bind to the antibodies (or antigens) in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

Figures 2A, 2B:
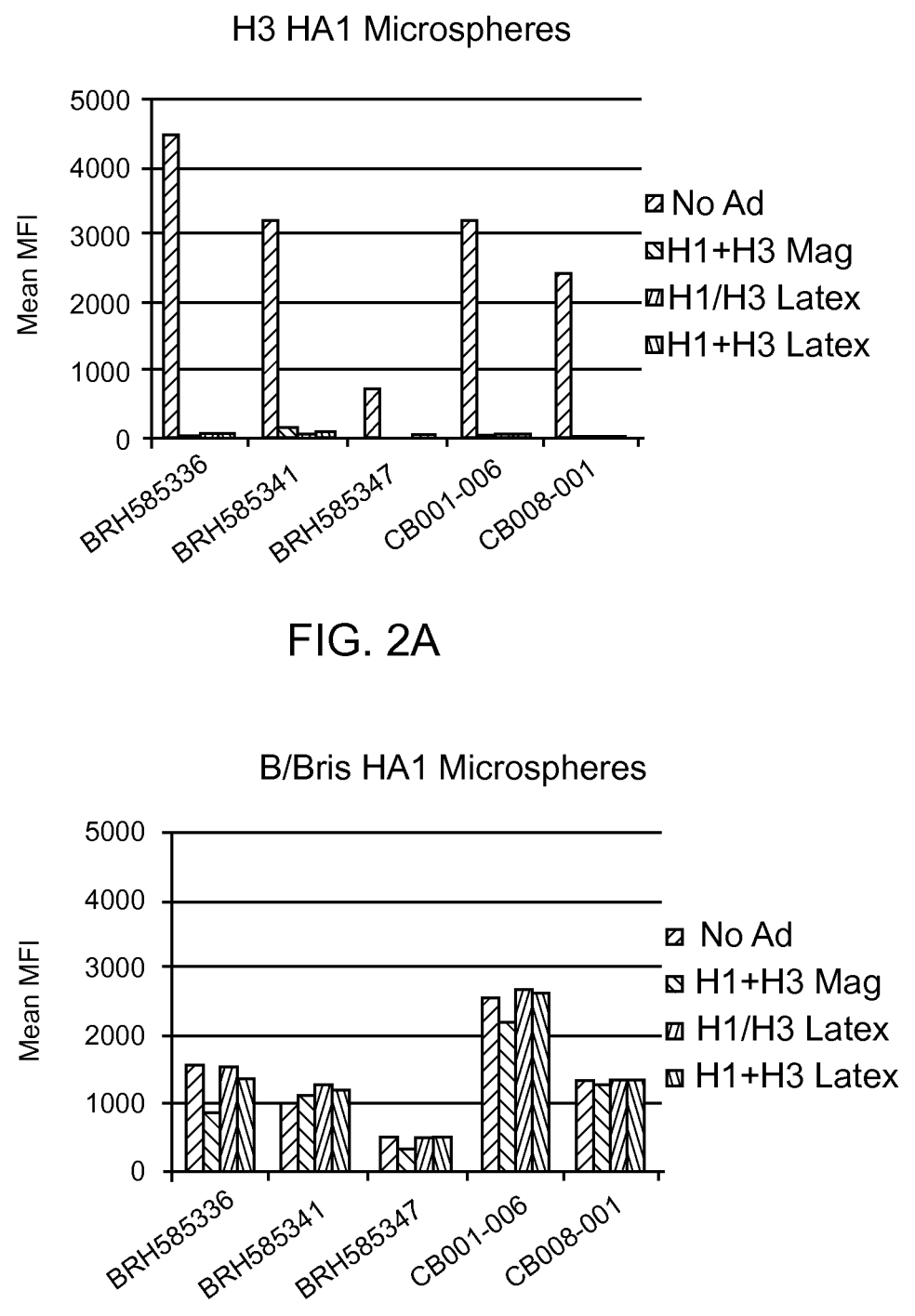

Turning to FIG. 2A, it can be seen that the apparatus of FIGS. 1, 1A and 1B can provide improved test results relative to a standard dual path platform apparatus such as described and shown in previously incorporated U.S. Pat. No. 7,189,522. In particular, three sets of five test apparatus such as described above with reference to FIGS. 1, 1A and 1B were prepared with a second conjugate pad 32b provided with a conjugate 41 having H3 and H1 flu-A antigen conjugated with beads, and a DPP test line provided with Flu A antigens. One set of five apparatus utilized magnetic beads separately conjugated with H1 antigen and H3 antigen (H1+H3 Mag). A second set utilized latex beads separately conjugated with H1 and H3 antigen (H1+H3 Latex). A third set utilized latex beads with combined H1 and H3 conjugation (H1/H3 Latex). Similarly, a set of devices such as described and shown in previously incorporated U.S. Pat. No. 7,189,522 were provided (No Ad) with a test line having the same flu-A antigens. Test samples from five different individuals having H3 antibodies were prepared and applied to the second flow paths of the sets of devices described above with reference to FIGS. 1, 1A and 1B and the set of devices of U.S. Pat. No. 7,189,522. After waiting for the samples to reach the test sites, buffer was added to the first migration path of each device to move the marker conjugate to the test sites. The intensity of the signals at each test site was measured and plotted. As seen in FIG. 2A, the test lines of the five standard dual path platform apparatus (No Ad) showed a relative intensity (with a digital reader) ranging from about 700 to well over 4000 compared to a relative intensity of nearly zero for the apparatus of FIGS. 1, 1A, and 1B utilizing the beads for the magnetic and latex beads. These test show that the apparatus of FIG. 1 is successful in depleting the flu-A antibodies by utilizing the flu-A antigen—particle conjugate in the flow path of the sample. Where white particles are utilized, to the extent that any flu-A antigen—particle conjugate was carried down to the test site and captured there, the white particle prevents the conjugate from being seen against the white background of card 38b over which the test line 50 is located. It should be appreciated that by depleting flu-A H1 and H3 (seasonal flu) with the latex conjugate system in the path of the sample, the sensitivity and specificity of the test with a test line for pandemic flu A will be increased because of the elimination of the cross-reactivity between the seasonal and pandemic flu A antigens.

In one embodiment, the conjugate in the sample flow path utilizes fragments or fractions of seasonal flu H1 and H3 conjugated to latex particles. The fragments are immunodominant portions of the particle that will not substantially cross-react with other flu antigens and are different from the H1 and H3 antibodies that might be used as capture antibodies at the test site in the membrane (the whole molecule of H1 and H3). As a result, when a test for pandemic flu is provided with a test line including pandemic flu antibodies, the H1 and H3 fragment conjugates will have minimal cross-reactivity with pandemic flu antigens resulting in a better detection of a pandemic flu at the test line.

Turning to FIG. 2*b*, other samples were prepared having flu-B/Bris antibodies. The samples were applied to a sets of the standard dual path platform apparatus such as described in previously incorporated U.S. Pat. No. 7,189,522 where the test line had flu-B/Bris antigen (No Ad) and to sets of devices such as shown in FIGS. 1, 1A and 1B where the second conjugate pad 32*b* was provided with a conjugate 41 having H1 and H3 flu-A antigens conjugated to beads, and a test line provided with flu-B/Bris antigens. As with tests of FIG. 2A, one set of apparatus utilized magnetic beads separately conjugated to H1 and H3 (H1+H3 Mag), a second set utilized 0.32 micron white latex beads separately conjugated (H1+H3 Latex), while a third set utilized the white latex beads with combined conjugation (H1/H3 Latex). As seen in FIG. 2B, the positive results at the test line of the apparatus 10 of FIG. 1 is just as strong as the test lines of the standard dual path platform apparatus showing that the conjugate 41 located in the second migration path did not interfere with the results, as the signals at the test lines were nearly the same for all tests of a particular sample. Taking FIGS. 2A and 2B together, it will be appreciated that the apparatus 10 of FIGS. 1, 1A, and 1B has higher sensitivity.

Turning now to FIG. 3, a kit 100 is seen that includes a water vial 101 with water 102, a vial 103 with freeze dried latex conjugate 104, a diluent vial 105 with a diluent 106, a blood collection and transfer device 107, four transfer pipettes 108*a*, 108*b*, 108*c*, 108*d*, and a filter chamber assembly 109. It will be appreciated that the kit could have different numbers of elements. Thus, rather than separately maintaining water and freeze dried latex conjugate, a "wet" latex conjugate may be stored utilizing water and/or diluent. Likewise, rather than maintaining a vial of diluent, diluent may be provided as part of the "wet" latex conjugate. Also, rather than utilizing four transfer pipettes, fewer transfer elements may be utilized. In one embodiment, kit 100 may be used in conjunction with an immunoassay device test cell such as device 10 of FIGS. 1, 1A, and 1B. In another embodiment, kit 100 may be used in conjunction with other immunoassay devices such as ELISA (enzyme-linked immunosorbent assay). In another embodiment, kit 100 may be used in conjunction with an immunoassay device test cell such as described in previously incorporated U.S. Pat. No. 7,189,522.

More particularly, the water 102 in vial 101 may be mixed with the freeze dried latex conjugate 104 in vial 103 by using a pipette 108*a* and transferring the water to the latex vial. The vial 103 may be inverted multiple times in order to cause the freeze dried latex conjugate to be reconstituted. The reconstituted latex may be stored in a refrigerator if desired. In one embodiment, the dried latex conjugate is a conjugate of one or more flu antigens such as H1 and H3 with microbeads of latex. The latex beads may be of an easily visible color, e.g., blue.

When it is desired to test a sample, the sample, e.g., blood, may be obtained from a patient in a desired manner, e.g., a fingerstick, utilizing a blood collection and transfer device 107 such as a Minivette POCT manufactured by Sarstedt, Newton, N.C. The blood sample may be transferred into the diluent vial 105 containing a diluent 106 such as heparin or EDTA. The reconstituted latex conjugate may then be transferred into the diluent vial 105 by using a pipette 108*b*, and the blood and reconstituted latex conjugate may be mixed by inverting multiple times over a period of time and also giving antibodies in the blood an opportunity to be captured by the latex conjugate. After sufficient mixing and a sufficient period of time, the contents of the sample diluent vial 105 may then be transferred with pipette 108*c* to a filter chamber 109 such as a GE Healthcare Life Sciences Mini-UniPrep filter chamber comprising a filter 109*a*, compressor 109*b*, plunger 109*c*, and a tube 109*d*, although other filter mechanisms could be utilized. Using the hand compressor 109*b* of the filter chamber, the filter 109*a* can be plunged into the sample mixture, and the filtered sample can be collected in the tube 109*d* of the filter chamber. It will be appreciated that the filter is chosen to have pores that are smaller than the size of the latex conjugate beads. As a result, the conjugate beads (with captured antibodies, if any) are filtered out of the sample, and the sample (with antibodies that haven't been captured by the conjugate) with the previously added diluent and water will be caught in the tube 109*d*. Thus, while the contents of the sample diluent vial 105 that were transferred to the filter chamber 109 may have appeared to be dark blue (due to the blue latex conjugate and the blood), the contents of the tube 109*d* should be light red (the color of diluted blood). Regardless, it will be appreciated that the ligands that are related to but not the same as the ligands of interest will have been removed from the sample.

The contents of tube 109*d* are then transferred by pipette 108*d* and used in conjunction with an immunoassay device. In one embodiment, the immunoassay device is an otherwise prior art type device such as ELISA (enzyme-linked immunosorbent assay) or a LUMINEX assay sold by Thermo Fisher Sicentific, Holtsville, N.Y. When provided with a sample that is processed in this manner, the results of the ELISA and the LUMINEX devices are enhanced. In another embodiment, the immunoassay device to which the contents of tube 109*d* are transferred is an immunoassay device test cell such as described in previously incorporated U.S. Pat. No. 7,189,522 such as by applying a selected amount of the contents to the (second) location for receiving the liquid sample, waiting for the liquid sample to reach the test site via the second migration path, and then applying buffer or a buffer—conjugate subsystem to the first location to cause a conjugate to reach the test site via the first migration path. When provided with a sample that is processed as previously described, the results of the device described in previously incorporated U.S. Pat. No. 7,189,522 are enhanced.

In another embodiment, rather than utilizing a kit 100 with elements such as a water vial, a vial with freeze dried latex conjugate, a diluent vial, a filter chamber assembly, etc., the kit includes a conjugate which may be maintained in a wet form with or without buffer, or may be maintained in a freeze-dried conjugate format which may be reconstituted with water and/or a buffer solution. In one embodiment, the latex conjugate comprises white latex beads with antibodies or antigens conjugated thereto. The sample and conjugate are mixed together to permit the conjugate to deplete interfering antigens or antibodies. The mixed sample and conjugate may then be applied to an immunoassay device test cell such as described in previously incorporated U.S. Pat. No. 7,189,522 such as by applying a selected amount of the contents to the (second) location for receiving the liquid sample, waiting for the mixed sample and conjugate to reach the test site via the second migration path, and then applying buffer or a buffer—conjugate subsystem to the first location to cause a conjugate to reach the test site via the first migration path. When provided with a sample that is processed as previously described, the results of the device described in previously incorporated U.S. Pat. No. 7,189,522 are enhanced.

Figure 4A:
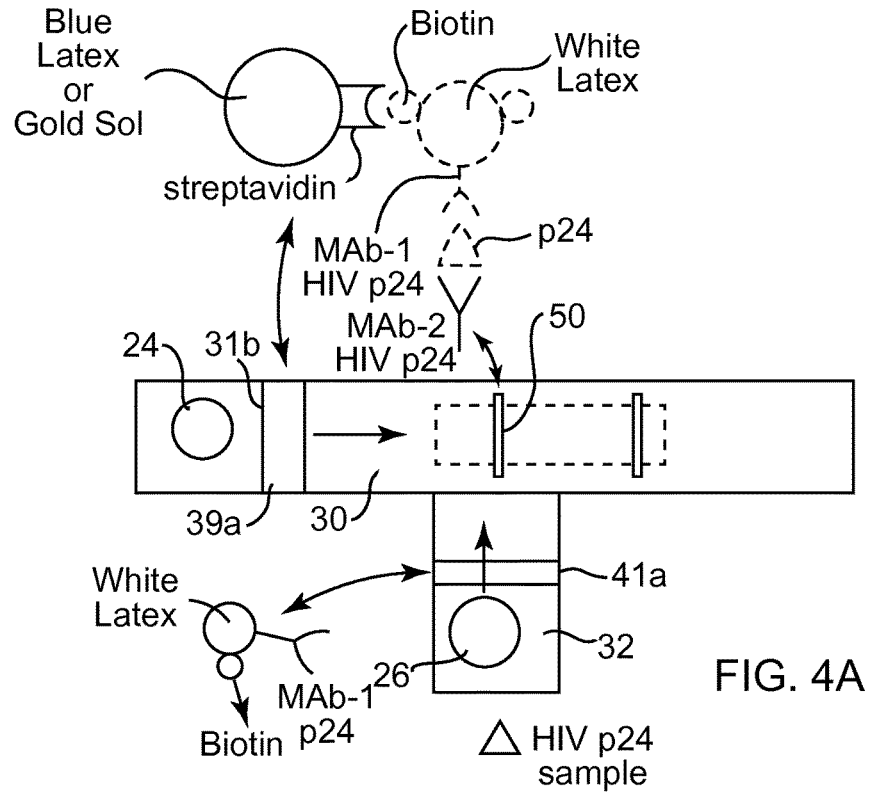
FIG. 4A is a diagram depicting a first alternative embodiment.
Figure 4B:
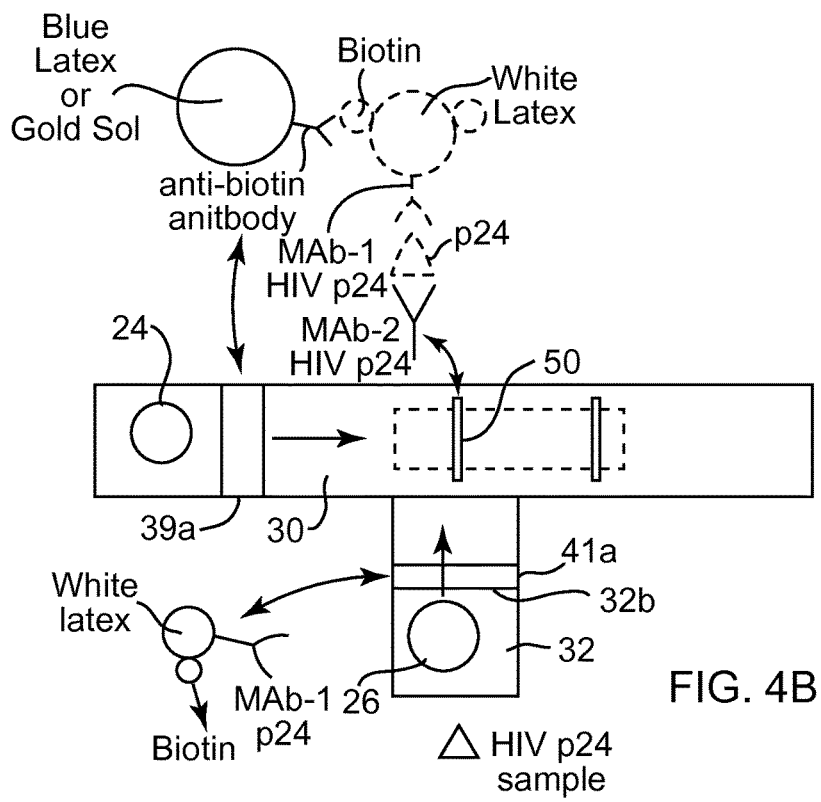
FIG. 4B is a diagram depicting a second alternative embodiment.
Figure 4C:
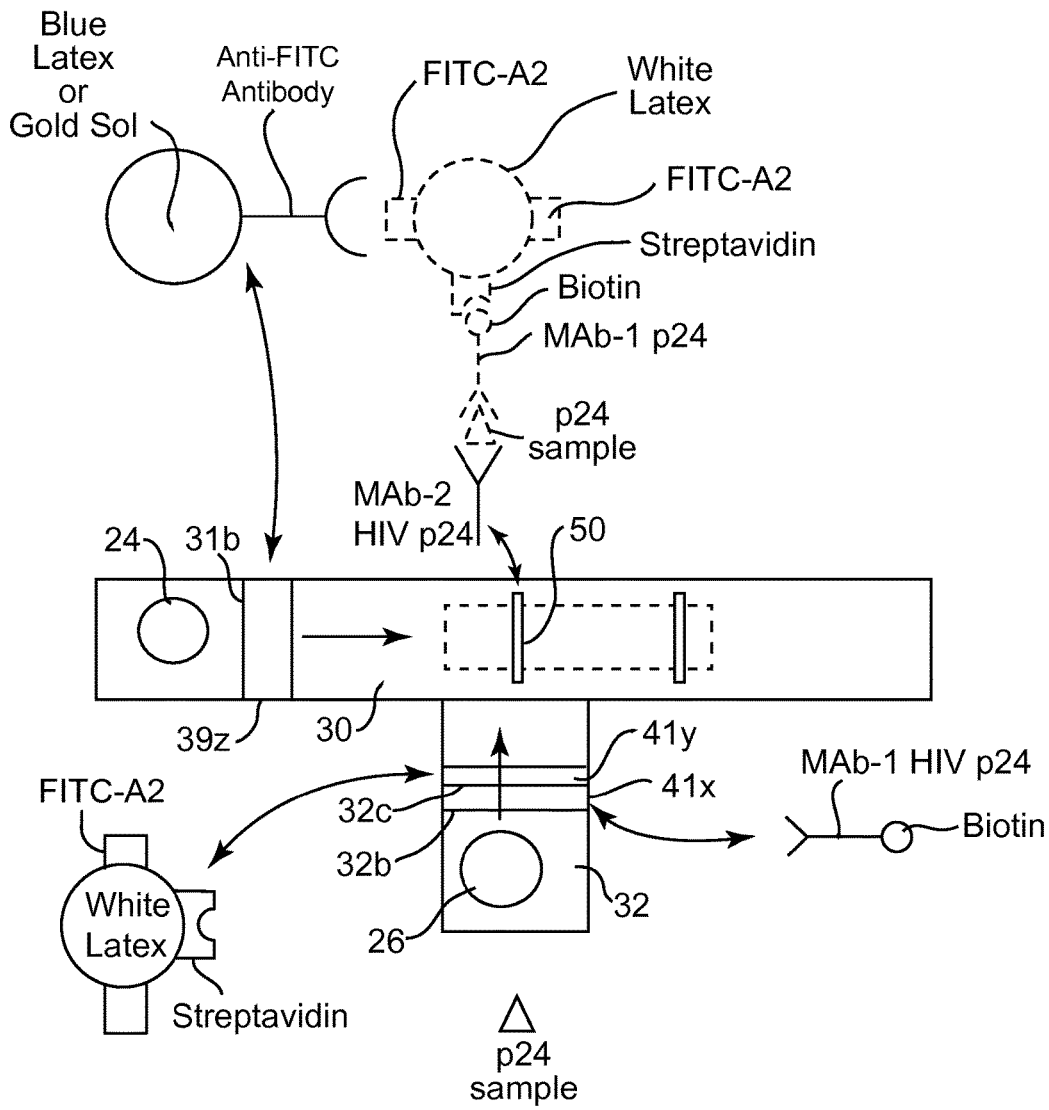
FIG. 4C is a diagram depicting a third alternative embodiment.

Turning to FIGS. 4A-4C, additional embodiments are provided that result in an apparatus having an enhanced test signal. FIGS. 4A-4C are described with reference to HIV test devices although they are not limited thereto. The embodiments of FIGS. 4A and 4B are similar to that of FIGS. 1, 1A, and 1B except that the conjugates provided on pads 31$b$ and 32$b$ are different, and the immobilized test line antigen is an HIV antibody rather than a flu antibody. More particularly, in FIG. 4A, conjugate 41$a$ in the sample migration path 32 includes a latex particle (e.g., a white latex) to which a MAb-1 p24 antibody and a first interim binding agent (e.g., biotin antigen) are conjugated. The test line 50 is provided with a monoclonal anti-HIV antibody protein (MAb-2 p24). The buffer-conjugate subsystem of the first migration path 30 is provided with a conjugate 39$a$ including a marker (e.g., blue latex or gold sol) and a second interim binding agent (e.g., streptavidin) conjugated thereto that is chosen to bind to the first interim binding agent. With the provided system, when a sample containing HIV p24 antigen is added to the test apparatus through hole 26, the HIV p24 antigen in the sample will bind to the MAb-1 p24 of the conjugate, and the sample with the antigen of interest bound to the conjugate will travel to the test line 50 where the p24 antigen of the sample will be caught by the MAb-2 p24 antibody at the test line. When buffer is added to the first sorbent strip through hole 24, the marker conjugate will move to the test line where the first interim binding agent will bind with the second interim binding agent, and the marker will appear at the test line.

The embodiment of FIG. 4B is very similar to the embodiment of FIG. 4A, except that instead of the second interim binding agent of conjugate 39$a$ being a tetrameric protein such as streptavidin, the second interim binding agent is an anti-biotin antibody. As a result, where the sample contains HIV p24 antigen, at the test line, the HIV p24 antigen will be retained at the test line by the MAb-2 p24 antibody of the test line, and the marker conjugate will bind to the first conjugate because the antibiotin antibody will bind to the biotin that is part of the first conjugate as seen in FIG. 4B The embodiment of FIG. 4C is likewise similar to the embodiments of FIGS. 4A and 4B, except that a double interim binding arrangement is utilized. More particularly, the second sorbent material 32 is provided with a pad 32$c$ in addition to pad 32$b$. In one embodiment, pad 32$b$ is provided with MAb-1 HIV p24 antigen conjugated with biotin 41$x$ with the biotin acting as a first interim binding agent of a first pair, and pad 32$c$ is provided with particles such as a white latex particles conjugated with streptavidin and a secondary antigen such as FITC-A2 (fluorescein isothiocyanate) 41$y$. The streptavidin of particles 41$y$ act as a second interim binding agent of a first pair, and the FITC-A2 acts as a first interim binding agent of a second pair. Pad 31$b$ is provided with a conjugate 39$z$ having a marker to which is conjugated an anti-FITC antibody which acts as a second interim binding agent of a second pair. With the provided arrangement, if the sample contains a p24 antigen, when the sample is added to the second sorbent material 32, the p24 antigen will attach to the MAB-1 HIV p24 antibody with biotin at pad 32$b$. As the sample progresses along its migration path to pad 32$c$, the biotin will bind to the streptavidin of the conjugate 41$y$; i.e., the first and second interim binding agents of the first pair bind together, and the complex of the p24 antigen—MAB-1 HIV p24 antibody with biotin—streptavidin/white latex/FITC antigen conjugate 41$y$ will move to the test site that includes MAB-2 HIV p24 antibody. At the test site, the p24 antigen of the sample will bind to the MAB-2 HIV p24 antibody of the test site, and the entire previously-described complex will be held at the test site. When buffer is then added to the first migration path and marker-anti-FITC antibody conjugate is moved to the test site, the anti-FITC antibody will bind to the FITC-A2 being held at the test site; i.e., the first and second interim binding agents of the second pair bind together. As a result, the marker will be held at the test line and provide a positive test result.

The embodiments of FIGS. 4A-4C may all be used in conjunction with a sample being provided directly to the apparatus or with a sample such as the previously described sample contained in tube 109$d$ which has resulted from a sample having been previously mixed with a depletion conjugate for antigens or antibodies different from but related to the antigen or antibody of interest and then filtered. In all cases, the molecules and conjugates on pads 32$b$ and 31$b$, and 32$c$ (if present) are appropriately selected, as are the molecules on the test line 50 and the freeze-dried depletion conjugate 104.

There have been described and illustrated herein several embodiments of immunoassays and methods of their use. While particular embodiments have been described, it is not intended that the claims be limited thereto, as it is intended that the claims be as broad in scope as the art will allow and that the specification be read likewise. Thus, while the specification discusses ligand binding using antigen/antibody reactions, other ligand binding mechanisms such as aptamer binding, nucleic acid binding, enzymatic binding, etc. may also be used. Also, while the test cells are described as having a single line for testing for a single ligand, it will be appreciated that two or more lines may be utilized for testing for more than one ligand. Further, while the test cells are described as having holes in the top wall of a housing for receiving the sample and the buffer-solution or buffer-conjugate subsystem, it will be appreciated that one or both holes may be provided in the end wall or side wall of the housing. Similarly, while the sorbent material was described as preferably including a thin plastic backing, it will be appreciated that the plastic backing could be provided only at certain locations or not be provided at all. Where only partial backings or no backings are provided, the test and control sites can be located on either or both sides of the sorbent material. Further yet, while a test strip and control strip are shown is being rectangular in configuration (i.e., lines), it will be appreciated that the test and control sites can be configured differently such as in circles, squares, ovals, a broken line, etc. In fact, the test site and control site can be configured differently from each other.

Those skilled in the art will also appreciate that the housing may be modified in additional ways to include separate windows for each test line. Also, while the embodiments were described in conjunction with the use of a buffer solution which is added to the migration path of the conjugate and optionally to the migration path of the sample, it will be appreciated that that one or more buffers may be chosen as desired to be added to the migration paths depending upon the test or tests to be conducted. Thus, buffers such as phosphate buffers or TRIS (tris hydroxymethylaminomethane) buffers are often utilized. However, the embodiments are intended to encompass the use of any diluent including water. In addition, the diluent may, if needed, may be added to and mixed with the sample prior to adding the sample to the sorbent material or the sample may be deposited first and the diluent may be added thereafter. Likewise, any diluent capable of causing the conjugate of the "non-sample" path to migrate may be utilized, and may be premixed with the conjugate in a liquid conjugate system, or provided to the migration path for the conjugate in a dry conjugate system.

Those skilled in the art will also appreciate that while the embodiments were described with particular reference to detection of a flu antibody and HIV p-24 antigen, the apparatus and methods may be useful in detection of other antibodies or antigens whether human or animal. Also, while the embodiments were described with particular reference to the use of blood as a sample, it will be appreciated that other body fluids or excretions, or blood portions may be utilized including, but not limited to urine, feces, saliva, spitum, blood serum (plasma), etc. It will therefore be appreciated by those skilled in the art that yet other modifications could be made without deviating from the spirit and scope of the claims.

What is claimed is:

1. A method for testing a sample for the presence of a first ligand, comprising:
   a) obtaining a test device having a first sorbent strip having a first location for receiving a solution and defining a first migration path, a marker conjugate located on or in said first migration path, said marker conjugate adapted to bind to said first ligand, a second sorbent strip distinct from said first sorbent strip and having a second location for receiving the liquid sample and defining a second migration path, depletion molecules located on or in said second migration path wherein said depletion molecules include an immobilized ligand-binding element adapted to bind to second ligands that are different from but related to said first ligand, and a test site located on or in one at least one of said first sorbent strip and said second sorbent strip, said test site having an immobilized ligand-binding mechanism for said first ligand, and said first and second sorbent strips touching each other at the test site location, wherein said second location is removed from said test site such that sample applied to said second location requires time to migrate to said test site and does not immediately wet said test site;
   b) applying the sample to said second location;
   c) after said applying the sample, applying a solution to the first location to cause said marker conjugate to migrate along said first migration path; and
   d) inspecting said test site to determine an indication the presence or lack thereof of the first ligand in the sample, wherein
   said depletion molecules comprises a conjugate including an antigen or antibody for the second ligand and particles that are not readily seen by the human eye against a background of said test site,
   said test device has a housing defining a first opening adjacent said first location, a second opening adjacent said second location, and a window adjacent said test site through which said test site is viewable,
   said applying the sample comprises depositing the sample through said second opening to said second location,
   said applying the solution comprises depositing the solution through said first opening to said first location,
   said inspecting comprises inspecting through said window,
   said first ligand is a first flu antibody, and
   said second ligand is a second flu antibody different than said first flu antibody.

2. A method according to claim 1, wherein:
said first flu antibody is a pandemic flu antibody; and
said second flu antibody is a non-pandemic flu antibody.

* * * * *